US011547459B2

(12) United States Patent
Ahn

(10) Patent No.: US 11,547,459 B2
(45) Date of Patent: Jan. 10, 2023

(54) SPINAL PLATE SYSTEM FOR INTERVERTEBRAL BODY FIXATION

(71) Applicants: Kyoung Gee Ahn, Seoul (KR); GBS Commonwealth Co., Ltd., Seoul (KR); PMT Republic, Inc., Walnut, CA (US)

(72) Inventor: Kyoung Gee Ahn, Seoul (KR)

(73) Assignee: Kyoung Gee Ahn, Walnut, CA (US)

(*) Notice: Subject to any disclaimer, the term of this patent is extended or adjusted under 35 U.S.C. 154(b) by 186 days.

(21) Appl. No.: 16/943,013

(22) Filed: Jul. 30, 2020

(65) Prior Publication Data

US 2021/0038272 A1 Feb. 11, 2021

(30) Foreign Application Priority Data

Aug. 7, 2019 (KR) .......................... 10-2019-0095913

(51) Int. Cl.
*A61B 17/80* (2006.01)
*A61B 17/86* (2006.01)
*A61B 17/70* (2006.01)
*A61B 17/00* (2006.01)

(52) U.S. Cl.
CPC ........ *A61B 17/866* (2013.01); *A61B 17/7059* (2013.01); *A61B 2017/00862* (2013.01); *A61B 2017/8655* (2013.01)

(58) Field of Classification Search
CPC .............. A61B 17/7059; A61B 17/8033–8052
See application file for complete search history.

(56) References Cited

U.S. PATENT DOCUMENTS

| 6,793,658 | B2* | 9/2004 | LeHuec | A61B 17/1728 606/280 |
| 9,381,093 | B1* | 7/2016 | Morris | A61F 2/44 |
| 10,064,666 | B2* | 9/2018 | Dunaway | A61B 17/80 |
| 2005/0283152 | A1* | 12/2005 | Lindemann | A61B 17/8042 606/295 |
| 2011/0029023 | A1* | 2/2011 | Tornier | A61B 17/8042 606/289 |
| 2012/0065690 | A1* | 3/2012 | Perrow | A61B 17/8042 606/294 |
| 2013/0204300 | A1* | 8/2013 | Michelson | A61B 17/8042 606/246 |
| 2017/0196606 | A1* | 7/2017 | Cianfrani | A61B 17/8605 |

FOREIGN PATENT DOCUMENTS

KR 10-0823791 B1 4/2008

* cited by examiner

*Primary Examiner* — Eduardo C Robert
*Assistant Examiner* — Steven J Cotroneo
(74) *Attorney, Agent, or Firm* — Novick, Kim & Lee PLLC; Jae Youn Kim

(57) ABSTRACT

A spinal plate system that makes it possible to check the extent to which a screw for anchoring the device to a vertebra is inserted in the vertebra is proposed. The spinal plate system includes a fixing plate having a plurality of first fastening holes formed through a surface thereof, a plurality of screws, which are respectively inserted into the plurality of first fastening holes and are threadedly coupled to a vertebra, and a locking rivet, which is disposed adjacent to the plurality of fastening holes and which comes into contact with first ends of the plurality of screws so as to hold the plurality of screws, the locking rivet including an elastic portion, which is elastically deformed by the plurality of screws when the screws are inserted into the fixing plate and which is elastically restored after the screws are completely inserted to a predetermined depth.

7 Claims, 7 Drawing Sheets

SPINAL PLATE SYSTEM FOR INTERVERTEBRAL BODY FIXATION

CROSS-REFERENCE TO RELATED APPLICATIONS

The instant application claims priority to Korean patent application No. 10-2019-0095913 filed on Aug. 7, 2019, the disclosure of which is hereby incorporated by reference in its entirety.

BACKGROUND OF THE INVENTION

Field of the Invention

The present invention relates to a spinal plate system, and more particularly to a spinal plate system capable of making it possible to check the extent to which a screw for anchoring the device to a vertebra is inserted into the vertebra.

Description of the Related Art

Vertebrae are bones constituting the vertebral column, and connect cranial bones to pelvic bones so as to define the central axis of the human body and to support the human body. The vertebrae include cervical vertebrae, thoracic vertebrae, lumbar vertebrae, sacral vertebrae and the coccygeal vertebrae.

A vertebra, which has the above-described structure and functions, may be damaged or deformed by an external impact occurring during an accident or due to long periods of poor posture. In order to correct such a damaged or deformed vertebra, a spinal plate system, which is composed of a plate and screws, is used.

However, such a conventional spinal plate system has a problem in that it is difficult to check the extent to which a screw is rotated and inserted into a vertebra so as to anchor a plate to the vertebra.

Accordingly, even after a screw is completely inserted into a vertebra, an operator cannot confirm the complete insertion of the screw. Hence, there is a problem in that torque continues to be applied to the screw and the portion of the vertebra near the screw is damaged, thereby decreasing the coupling force between the device and the vertebra.

Furthermore, when the screw is not completely inserted into the vertebra in the interests of preventing damage to portion of the vertebra near the screw, there is also a problem in that the screw inserted into the vertebra is easily separable from the vertebra by movement of a joint, an impact, or the like.

The details described as the background art are intended merely for the purpose of promoting an understanding of the background of the present invention and should not be construed as an acknowledgment of the prior art that is previously known to those of ordinary skill in the art.

SUMMARY OF THE INVENTION

Therefore, the present invention has been made in view of the above problems, and it is an object of the present invention to provide a spinal plate system capable of making it possible to check the extent to which a screw is inserted into a vertebra when the screw is completely inserted into the vertebra.

It is another object of the present invention to provide a spinal plate system capable of preventing a screw from being pulled out of a vertebra after the screw is inserted into the vertebra.

The technical objects intended to be accomplished by the present invention are not limited to the above-mentioned objects, and other technical objects not mentioned herein will be apparent to those skilled in the art from the following disclosure.

In accordance with an aspect of the present invention, the above and other objects can be accomplished by the provision of a spinal plate system including a fixing plate having a plurality of first fastening holes formed through a surface thereof, a plurality of screws, which are respectively inserted into the plurality of first fastening holes and are threadedly coupled to a vertebra, and a locking rivet, which is disposed adjacent to the plurality of fastening holes and which comes into contact with first ends of the plurality of screws so as to hold the plurality of screws, the locking rivet including an elastic portion, which is elastically deformed by the plurality of screws when the screws are inserted into the fixing plate and which is elastically restored after the screws are completely inserted to a predetermined depth.

In the spinal plate system according to an embodiment of the present invention, the locking rivet may be disposed between at least two first fastening holes.

In the spinal plate system according to an embodiment of the present invention, the fixing plate may have a second fastening hole into which the locking rivet is inserted, and the locking rivet may include an engagement portion rotatably fitted in the second fastening hole, and a locking portion coupled to a first end of the engagement portion, the locking portion being disposed on the surface of the fixing plate so as to prevent separation of the plurality of screws after the screws are completely inserted into the plurality of first fastening holes.

In the spinal plate system according to an embodiment of the present invention, after the plurality of screws are completely inserted, the locking portion may be rotated about the engagement portion and may be disposed on first ends of the screws, thereby preventing separation of the screws.

In the spinal plate system according to an embodiment of the present invention, the elastic portion may be positioned at the first end of the engagement portion so as to be flush with the locking portion.

In the spinal plate system according to an embodiment of the present invention, the elastic portion may have a slit, which is open at a portion thereof.

In the spinal plate system according to an embodiment of the present invention, the elastic portion and the locking portion may be provided in accordance with the number and positions of the plurality of screws, which come into contact therewith, and may be alternately arranged about the engagement portion.

In the spinal plate system according to an embodiment of the present invention, the elastic portion may be configured to have a ring shape, and may be disposed between the locking portion and the surface of the fixing plate.

In the spinal plate system according to an embodiment of the present invention, the locking portion may include a plurality of locking portions, which are provided in accordance with the number and positions of the plurality of screws, which come into contact therewith, and which are arranged at predetermined intervals about the engagement portion.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
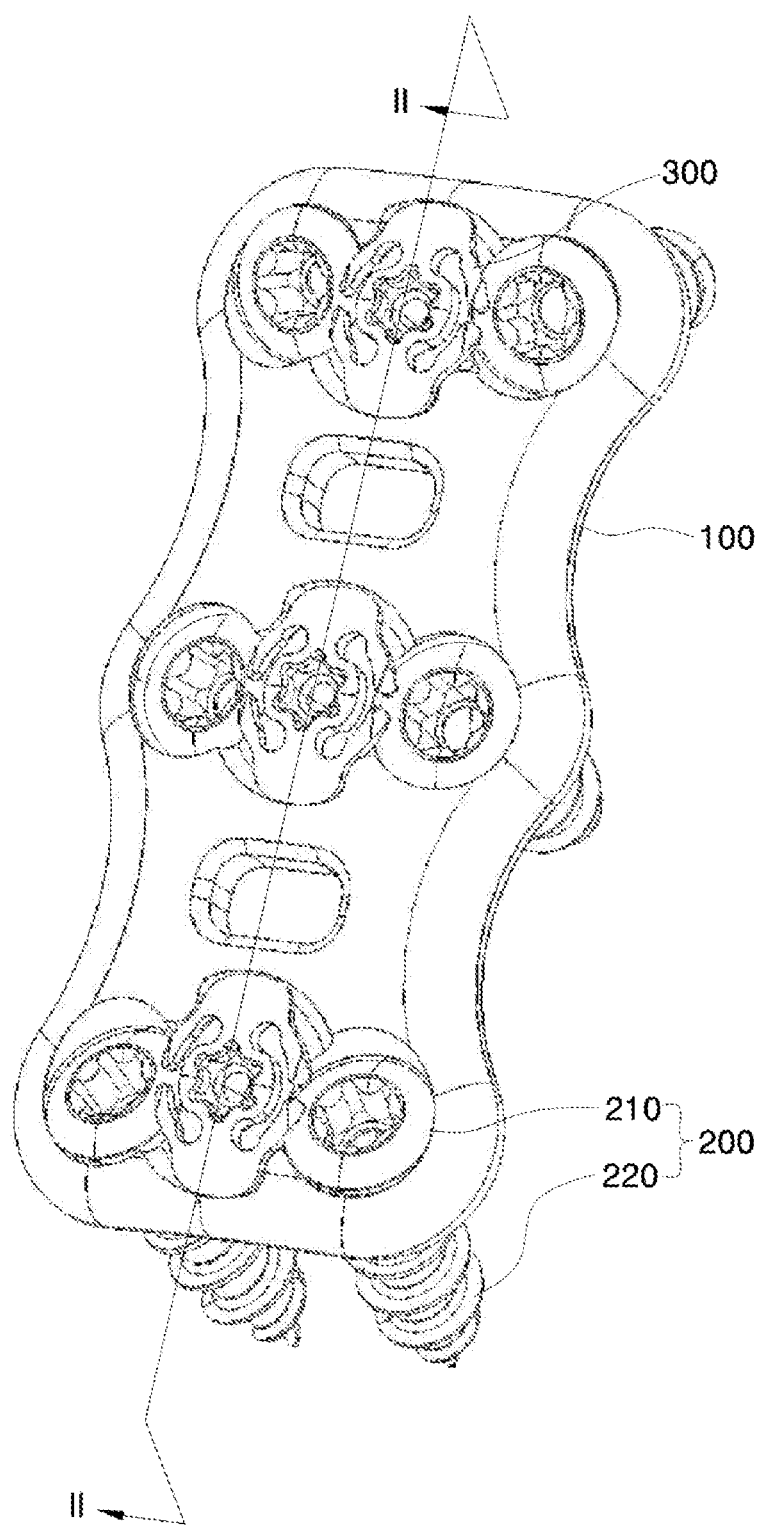
FIG. 1 is a perspective view of a spinal plate system according to a first embodiment of the present invention.

Hereinafter, a spinal plate system according to an embodiment of the present invention will be described in detail with reference to the accompanying drawings. However, the present invention may be embodied in many different forms, and should not be construed as being limited to the embodiments set forth herein. Rather, these embodiments are provided so that this disclosure will be thorough and complete, and will fully convey the scope of the disclosure to those skilled in the art.

It will be understood that, when a part is represented as "including" a component throughout this specification, the term "include" indicates that the component may further include other components, and does not preclude such other components unless otherwise indicated. Furthermore, if it is described that a component is formed on an object, it should be understood that the component is provided on the top or bottom of the object and that the component is not necessarily positioned on the top of the object based on the direction of gravitational force.

Preferred embodiments of the present invention are now described with reference to the accompanying drawings. It should be noted that the same reference numerals will refer to the same or like parts throughout the drawings. Furthermore, if it is decided that a detailed description of known functions or configurations related to the invention would make the subject matter of the invention unclear, such detailed description is omitted. For clarity of description, the shapes and sizes of some of the components in the drawings may be exaggerated or schematically illustrated.

Figure 2:
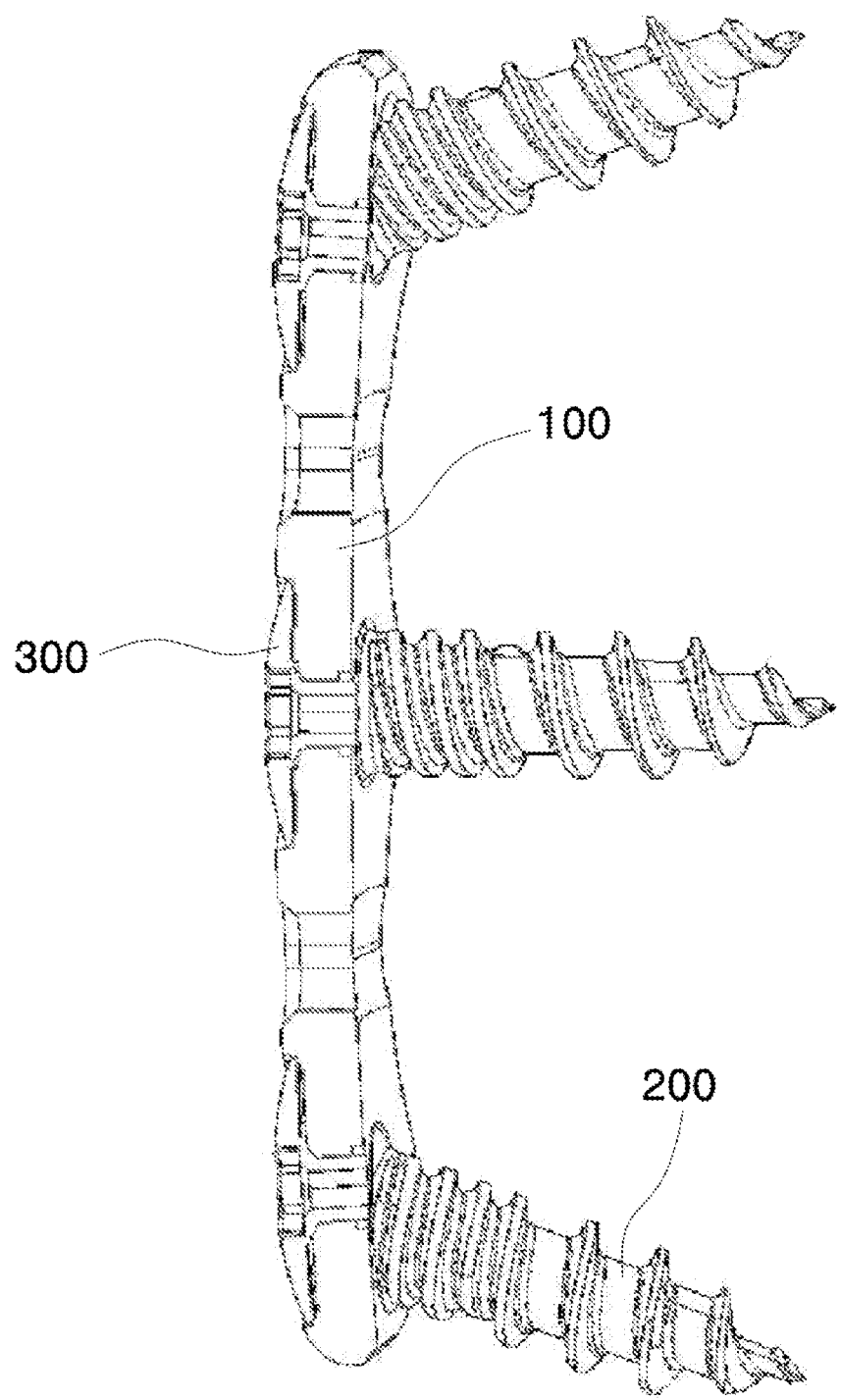
FIG. 2 is a longitudinal cross-sectional view of the spinal plate system, taken along line II-II in FIG. 1.
Figure 3:
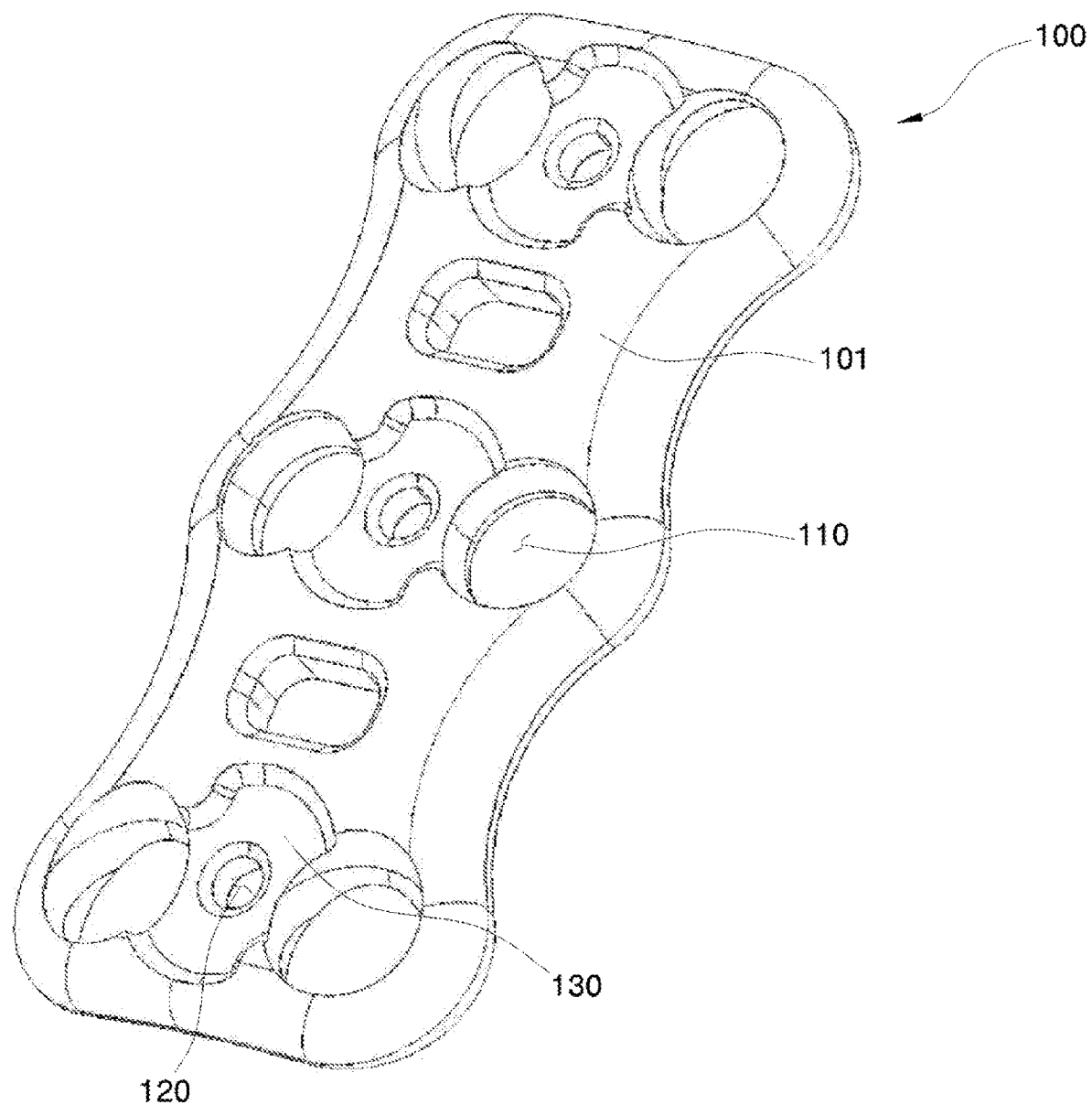
FIG. 3 is a perspective view illustrating a fixing plate of the spinal plate system according to the first embodiment of the present invention.

FIG. 1 is a perspective view of a spinal plate system according to a first embodiment of the present invention. FIG. 2 is a longitudinal cross-sectional view of the spinal plate system, taken along line II-II in FIG. 1. FIG. 3 is a perspective view illustrating a fixing plate of the spinal plate system according to the first embodiment of the present invention.

Referring to FIGS. 1 to 3, the spinal plate system according to the first embodiment of the present invention includes a fixing plate 100, screws 200 and locking rivets 300.

The spinal plate system is a device that is configured to anchor two or more vertebrae to each other with the aim of minimizing vertebral mobility and thus performing medical treatments and orthopedics for various vertebral diseases. Here, the term "vertebra" refers to any bone structure constituting a vertebral column, and the vertebrae may include all of the cervical vertebrae, the thoracic vertebrae, the lumbar vertebrae, the sacral vertebrae and the coccygeal vertebrae.

The fixing plate 100 is a structure configured to connect or anchor adjacent vertebrae, which are damaged or deformed, in order to fix the vertebrae and prevent displacement of the vertebrae.

The fixing plate 100 is configured to have a size sufficient to cover a plurality of vertebrae, particularly at least two vertebrae, and to extend in the direction of the spine. The fixing plate 100 may be generally concave at the region thereof that contacts the vertebrae to be orthopedically treated, so as to correspond to the shapes of the vertebrae. The fixing plate 100 may be made of an environmentally friendly material such as titanium, a titanium alloy or stainless steel.

The fixing plate 100 has a plurality of first fastening holes 110, which are formed through the surface 101 thereof. The screws 200 are inserted into the first fastening holes 110 so as to anchor the fixing plate 100 to a vertebra. The first fastening holes 110 may be arranged in two rows in the longitudinal direction of the fixing plate 100 such that a pair of first fastening holes 110 is disposed in every horizontal row with a predetermined interval therebetween. In this embodiment, the first fastening holes 110 are arranged in two rows.

The screws 200 are respectively inserted into the plurality of first fastening holes 110 formed in the fixing plate 100 so as to anchor the fixing plate 100 to a vertebra. The screws 200 may also be made of an eco-friendly material such as titanium, a titanium alloy or stainless steel.

Each of the screws 200 may be provided at one end thereof with a head part 210 and at the other end thereof with a threaded part 220. The threaded part 220 is inserted into a vertebra through the first fastening hole 110, and the head part 210 enables the threaded part 220 to penetrate a vertebra by rotation thereof. The head part 210 may have a larger diameter than the threaded part 220, and may have the same length as that of the first fastening hole 110 so as to be embedded in the first fastening hole 110.

The screw 200 may be inclined relative to the fixing plate 100 such that the angle of inclination of the screw 200 is adjustable within an allowable range in a width direction or in the longitudinal direction of the fixing plate 100 in accordance with the angle at which the screw 200 is inserted into a vertebra. In this embodiment, the screws 200 disposed at two ends of the fixing plate 100 in the longitudinal direction are inclined outwards in the longitudinal direction of the screws 200.

The screw 200 may be embodied as an unfixed screw such that the screw 200 is freely rotatable in the first fastening hole 110 in the fixing plate 100 and is movable even after being inserted into the fixing plate 100, or may be embodied as a fixed screw such that the screw 200 is capable of being freely inclined before being inserted into the fixing plate 100 but is immovable after being completely inserted into the fixing plate 100.

Figure 4:
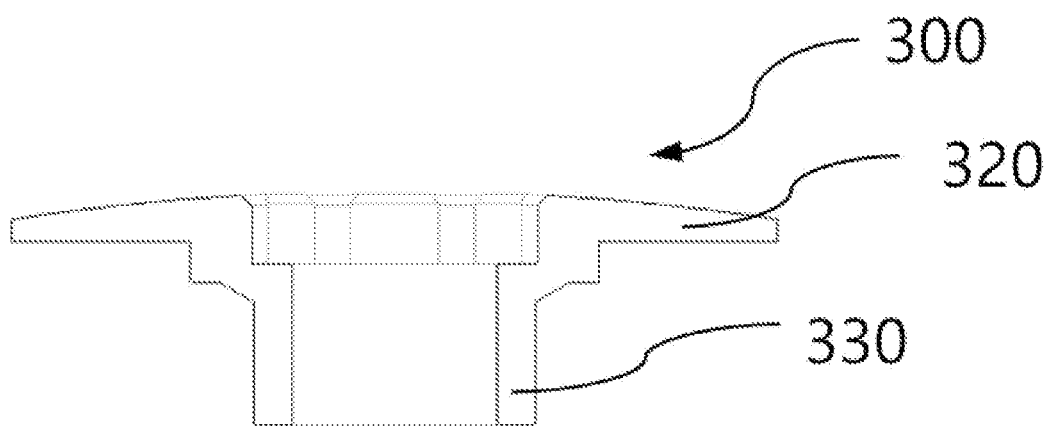
FIG. 4 is a cross-sectional view of a locking rivet of the spinal plate system according to the first embodiment of the present invention.
Figure 5:
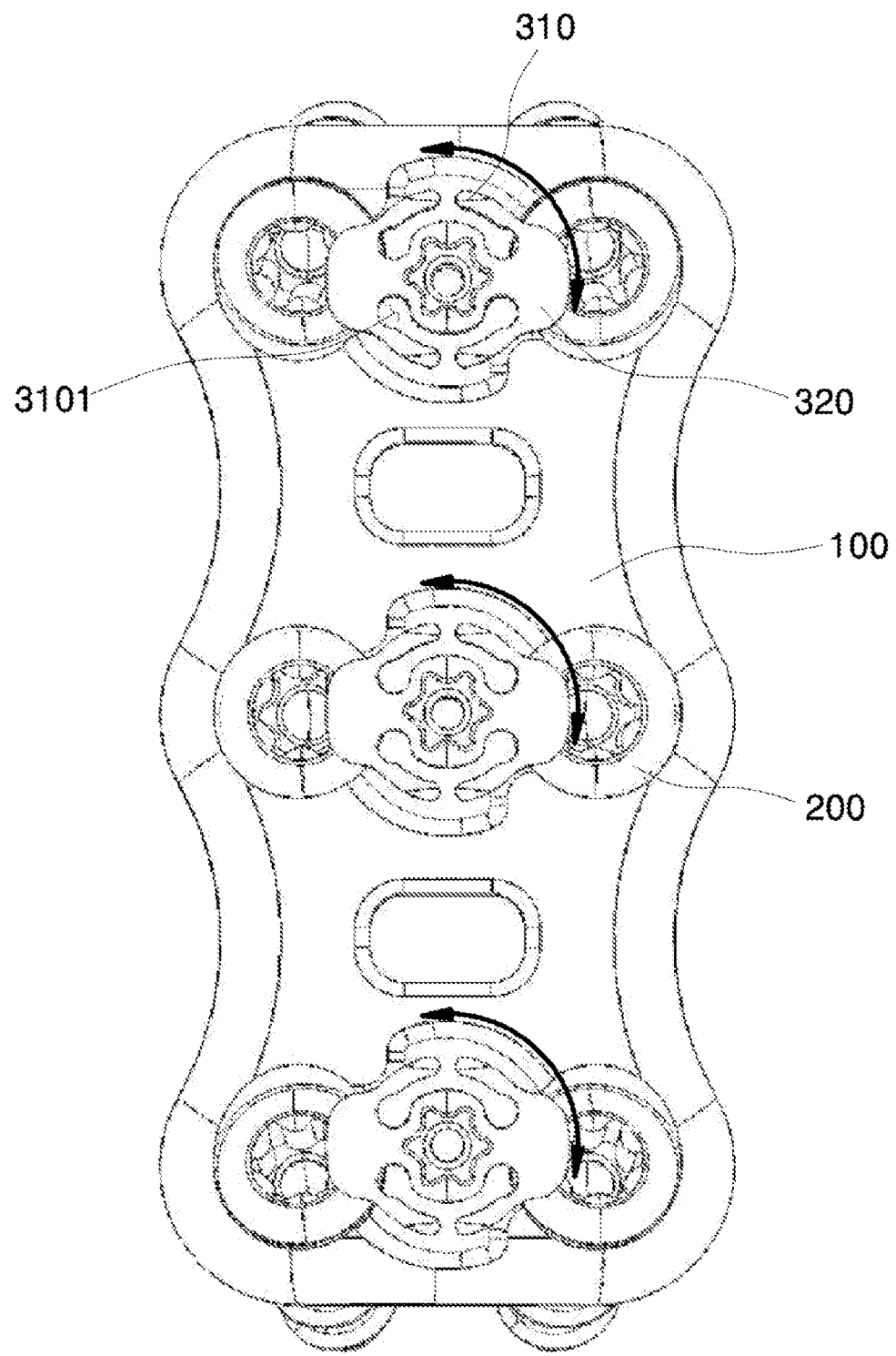
FIG. 5 is a plan view illustrating the spinal plate system according to the first embodiment of the present invention.

FIG. 4 is a cross-sectional view of the locking rivet of the spinal plate system according to the first embodiment of the present invention. FIG. 5 is a plan view illustrating the spinal plate system according to the first embodiment of the present invention. FIG. 5 illustrates the state in which the locking rivets 200 are rotated so as to securely hold the screws 200.

The locking rivets 200 are elements that are engaged with first ends of the screws 200 so as to hold the screws 200. Each of the locking rivets 300 may be disposed so as to be adjacent to a first fastening hole 110 or to be positioned between at least two first fastening holes 110. Although each of the locking rivets 300 is disposed so as to be in contact with a pair of screws 200, which are arranged in the width direction, the present embodiment may be variously modified such that the locking rivet 300 is disposed so as to be in contact with various numbers of screws 200, such as one screw 200 or three or four adjacent screws 200, without being limited thereto.

Elastic portions 310 of the locking rivet 300 are disposed at the inlet of the first fastening hole 110 so as to overlap a portion of the first fastening hole 110. When the screw 200 is inserted into the fixing plate 100 while pressing the elastic portions 310, the elastic portions 310 are elastically deformed. After the screw 200 is completely inserted to a predetermined depth, the elastic portions 310 are elastically restored.

Complete insertion of the screw 200 to the predetermined depth may be, for example, the state in which the threaded part 220 of the screw 200 is inserted into a vertebra through the first fastening hole 110 and the head part 210 is completely embedded in the first fastening hole 110. When the screw 200 is inserted into the first fastening hole 110, the elastic portions 310 are pressed and elastically deformed by the head part 210 of the screw 200. After the head part 210 of the screw 200 is embedded in the first fastening hole 110, the pressing force applied to the head part 210 is released and the elastic portions 310 are elastically restored.

The fixing plate 100 may have formed therein second fastening holes 120 into which the locking rivets 300 are inserted. The second fastening holes 120 may be arranged between the two longitudinal rows of first fastening holes 110 such that each of the second fastening holes 120 is positioned between a pair of corresponding first fastening holes 110. Consequently, each of the locking rivets 300 may also be disposed between a pair of corresponding first fastening holes 110, that is, a pair of corresponding screws 200.

Each of the locking rivets 300 may include an engagement portion 330, which is rotatably fitted in the second fastening hole 120, and locking portions 320 coupled to an end of the engagement portion 330, which is disposed on the surface 101 of the fixing plate 100 so as to prevent separation of the completely inserted screw 200.

The elastic portions 310 may be disposed at the one end of the engagement portion 330, and may be configured to be flush with the locking portions 320. The elastic portions 310 are also rotatable about the engagement portion 330 together with the locking portions 320. Each of the elastic portions 310 may have therein a slit 3101, which is open at a portion thereof. When the open slit 3101 is formed in the elastic portion 310, the elastic portion 310 is more easily and elastically deformable, and it is possible to easily visually check whether the elastic portion 310 is elastically deformed.

The elastic portions 310 and the locking portions 320 of the locking rivet 300 may be provided in accordance with the number and positions of the screws 200 adjacent to the locking rivet 300, and may be alternately arranged about the engagement portion 330 serving as the central shaft. Since one locking rivet 300 holds a pair of screws 200 in this embodiment, a pair of elastic portions 310 and a pair of locking portions 320 are alternately arranged about the engagement portion 330 such that the pair of elastic portions 310 face each other while the pair of locking portions 320 face each other.

When the screws 200 are completely inserted into the fixing plate 100, the locking portions 320 are rotated about the engagement portion 330 and are disposed on the first ends of the screws 200, thereby making it possible to prevent the screws 200 from being separated therefrom. When the head parts 210 are embedded in the first fastening holes 110 in the fixing plate 100, the locking portions 320 are rotated to thus cover portions of the head parts 210, thereby making it possible to prevent the head parts 210 from being separated from the first fastening holes 110.

The surface 101 of the fixing plate 100 has formed therein seat recesses 130, which are depressed therein and surround respective second fastening holes 120. Each of the recesses 130 receives therein the elastic portions 310 and the locking portions 320 such that the elastic portions 310 and the locking portions 320 are rotated in the recess 130.

Figure 6:
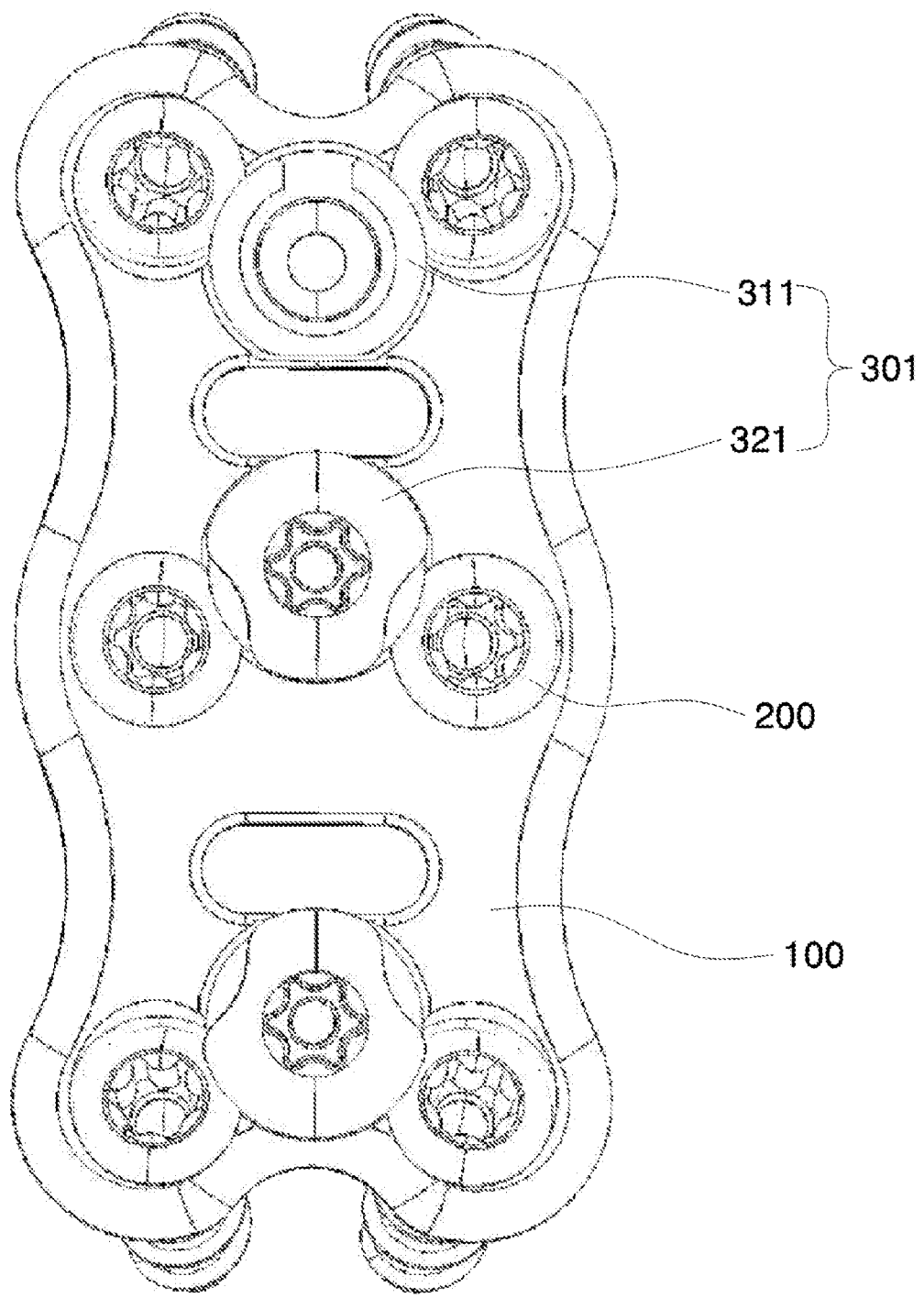
FIGS. 6 and 7 are plan views illustrating a spinal plate system according to a second embodiment of the present invention.
Figure 7:
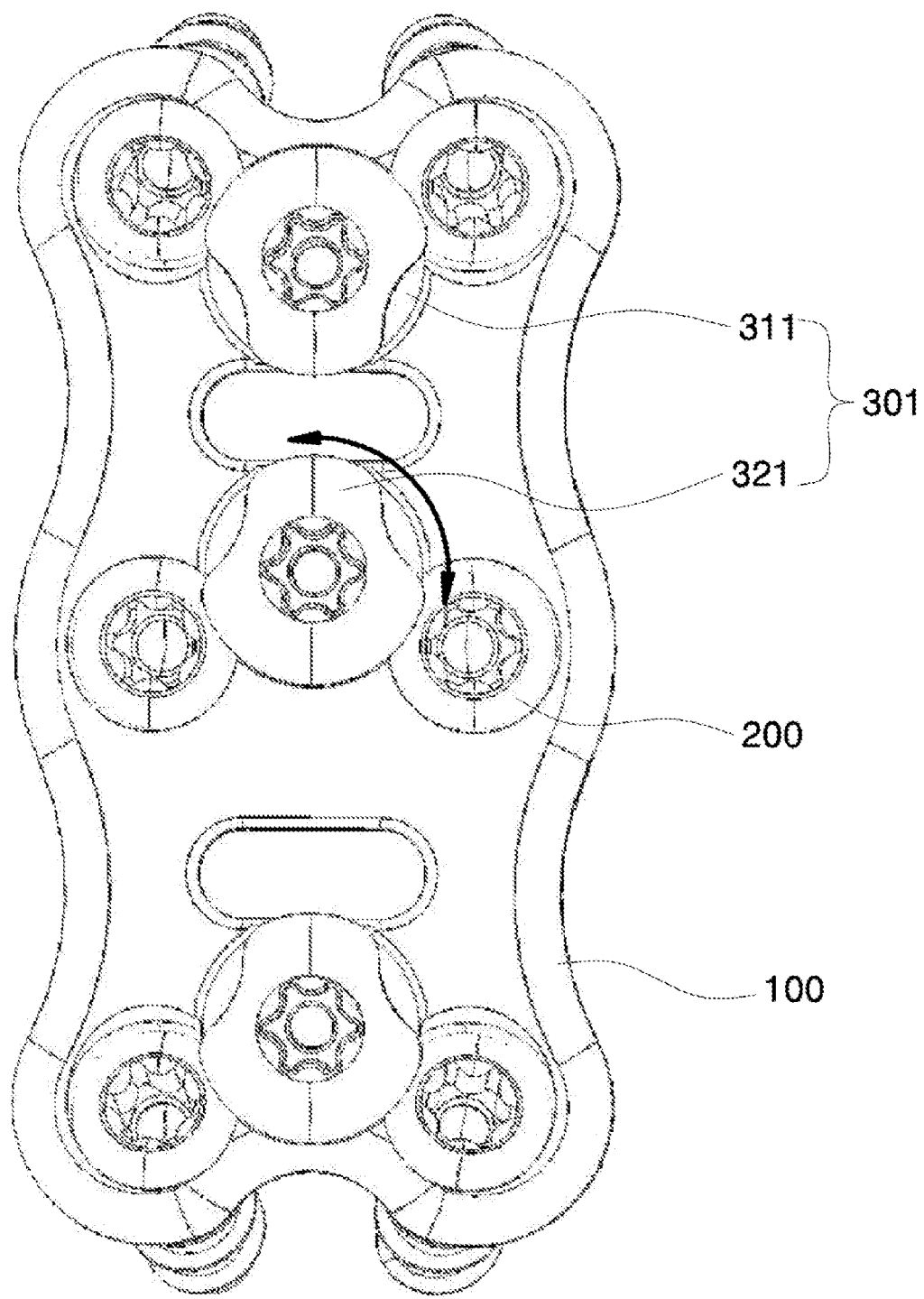

FIGS. 6 and 7 are plan views illustrating a spinal plate system according to a second embodiment of the present invention.

The spinal plate system according to the second embodiment of the present invention is constructed in a substantially similar manner to the spinal plate system according to the first embodiment of the present invention, with the exception that the locking rivets are modified. A description of components the same as those of the first embodiment is omitted, and the same components as those of the first embodiment are denoted by the same reference numerals.

An elastic portion 311 of a locking rivet 301 may be configured to have a ring shape. In the embodiment shown in the drawings, the elastic portion 311 is configured to be open at a portion thereof, that is, to have a C shape, and is disposed between locking portions 321 and the surface 101 of the fixing plate 100. Although the elastic portions are integrally formed with the locking portions 320 in the first embodiment, the elastic portion 311 is formed independently of the locking portions 321 in the second embodiment.

The two end portions of the C-shaped elastic portion 311 are disposed at the inlets of the first fastening holes 110 so as to overlap portions of the first fastening holes 110. The elastic portion 311 is received in the recess 130 formed in the surface 101 of the fixing plate 100, and the locking portions 321 are then received in the recess 130 so as to be disposed on the elastic portion 311.

As long as the elastic portion 311 is constructed independently of the locking portions 321 and is elastically pressed by the screw 200, the elastic portion 311 may be configured to have any shape. For example, the elastic portion 311 may be embodied as a retaining ring in which the two ends thereof overlap each other and are elastically deformed.

When the screw 200 is inserted into the fixing plate 100, the two end portions of the C-shaped elastic portion 311 are pressed and elastically deformed by the head part 210 of the screw 200. After the head part 210 of the screw 200 is embedded in the first fastening hole 110, the pressing force applied to the elastic portion 311 by the head part 210 is released, and the elastic portion 311 is thus elastically restored.

The locking portions 321 are constructed in accordance with the number and positions of the screws 200, and are arranged about the engagement portion 331 at predetermined intervals. Since the locking rivet 301 holds a pair of screws 200 in this embodiment, a pair of locking portions 321 is disposed so as to face each other.

Hereinafter, the operation of the spinal plate systems according to the embodiments of the present invention will be described with reference to the accompanying drawings.

Before the fixing plate 100 is placed on a vertebra to which the spinal plate system is to be mounted, the engagement portion 330 of the locking rivet 300 is fitted into the second fastening hole 120 such that the locking rivet 300 is positioned on the surface 101 of the fixing plate 100. In the second embodiment, the elastic portion 311, which is independently constructed, is positioned on the surface 101 of the fixing plate 100.

In order to anchor the fixing plate 100 to the vertebra, the screw 200 is inserted into the vertebra through the first fastening hole 110. At this time, the elastic portion 310 or 311 is pressed and elastically deformed by the head part 210 of the screw 200. As the screw 200 is further rotated and inserted, the head part 210 is embedded in the first fastening hole 110, and the pressing force applied to the elastic portion 310 or 311 is released, thereby allowing the elastic portion to be elastically restored.

Since an operator is able to visually or tactually check whether the elastic portion is elastically restored after the elastic portion 310 or 311 is elastically restored, it is possible to recognize that the screw 200 is properly inserted.

Subsequently, the locking rivet 300 is rotated such that the locking portions 321 are disposed on the head part 210 of the screw 200, thereby securely holding the screw 200 and thus preventing separation of the screw 200. Also in the second embodiment, the operation may be performed similarly to the first embodiment in such a manner as to insert the locking rivet 300 into the second fastening hole 120 and then to rotate the locking rivet 300.

As is apparent from the above description, according to the embodiments, when the screw is completely inserted into a vertebra, an operator is able to visually or tactually check the extent to which the screw is inserted, thereby preventing the vertebra from being injured.

Furthermore, it is possible to securely anchor the spinal plate system to a vertebra by preventing the screw from being pulled out of the vertebra.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A spinal plate system for intervertebral body fixation, comprising:
    a fixing plate having a plurality of first fastening holes formed through a surface thereof;
    a plurality of screws configured to be respectively inserted into the plurality of first fastening holes; and
    a locking rivet disposed adjacent to the plurality of first fastening holes and configured to be in contact with first ends of the plurality of screws so as to hold the plurality of screws,
    wherein the fixing plate has a second fastening hole into which the locking rivet is inserted,
    wherein the locking rivet includes:
    an engagement portion rotatably fitted in the second fastening hole;
    a locking portion coupled to a first end of the engagement portion, the locking portion being disposed on the surface of the fixing plate so as to prevent separation of the plurality of screws after the plurality of screws are completely inserted into the plurality of first fastening holes; and
    an elastic portion configured to be elastically deformed by the plurality of screws when the plurality of screws are inserted into the fixing plate and configured to be elastically restored after the plurality of screws are completely inserted to a predetermined depth, and
    wherein the locking portion is formed in an asymmetrical shape in which a width of one side is wider than a width of an opposite side of the one side with respect to an imaginary transverse line crossing a center of the locking portion, such that, when the locking portion is rotated around the engagement portion, the one side and the opposite side of the locking portion are vertically inverted, and then the one side of the locking portion is disposed on the first ends of the plurality of screws to prevent separation of the plurality of screws.

2. The spinal plate system according to claim 1, wherein the locking rivet is disposed between at least two first fastening holes.

3. The spinal plate system according to claim 1, wherein the elastic portion is positioned at the first end of the engagement portion so as to be flush with the locking portion.

4. The spinal plate system according to claim 3, wherein the elastic portion has a slit therein, the slit being open at a portion of the elastic portion.

5. The spinal plate system according to claim 3, wherein the elastic portion and the locking portion come into contact with each other, and are arranged about the engagement portion.

6. The spinal plate system according to claim 1, wherein the elastic portion has a ring shape, and is disposed between the locking portion and the surface of the fixing plate.

7. The spinal plate system according to claim 6, wherein the locking portion includes a plurality of locking portions, which are arranged at predetermined intervals about the engagement portion.

* * * * *